US012629440B2

(12) United States Patent
Pai et al.

(10) Patent No.: US 12,629,440 B2
(45) Date of Patent: May 19, 2026

(54) STERILIZATION APPARATUS

(71) Applicant: Plasma Bionics LLC, Stillwater, OK (US)

(72) Inventors: Kedar K. Pai, Stillwater, OK (US); Christopher T. Timmons, Stillwater, OK (US)

(73) Assignee: PLASMA BIONICS LLC, Stillwater, OK (US)

( * ) Notice: Subject to any disclaimer, the term of this patent is extended or adjusted under 35 U.S.C. 154(b) by 410 days.

(21) Appl. No.: 18/137,196

(22) Filed: Apr. 20, 2023

(65) Prior Publication Data

US 2023/0338596 A1     Oct. 26, 2023

Related U.S. Application Data

(60) Provisional application No. 63/333,303, filed on Apr. 21, 2022.

(51) Int. Cl.
| | |
|---|---|
| *A61L 2/14* | (2006.01) |
| *A61L 2/24* | (2006.01) |
| *A61L 2/26* | (2006.01) |
| A61L 103/15 | (2026.01) |

(52) U.S. Cl.
CPC .................. *A61L 2/14* (2013.01); *A61L 2/24* (2013.01); *A61L 2/26* (2013.01); *A61L 2103/15* (2026.01); *A61L 2202/11* (2013.01); *A61L 2202/122* (2013.01); *A61L 2202/14* (2013.01); *A61L 2202/15* (2013.01)

(58) Field of Classification Search
CPC .. A61L 2/14; A61L 2202/122; A61L 2202/24; A61L 2202/11; A61L 2/24; A61L 2202/14
See application file for complete search history.

(56) References Cited

U.S. PATENT DOCUMENTS

| | | | |
|---|---|---|---|
| 4,337,223 A | 6/1982 | Kaye |
| 4,410,492 A | 10/1983 | Kaye |
| 5,773,503 A | 6/1998 | Steen et al. |
| 5,906,802 A | 5/1999 | Langford |
| 6,312,645 B1 | 11/2001 | Lin et al. |

(Continued)

FOREIGN PATENT DOCUMENTS

| | | | |
|---|---|---|---|
| AU | 2014244561 A1 | 10/2014 |
| EP | 0336047 A1 | 10/1989 |
| WO | 2014043533 A1 | 3/2014 |

OTHER PUBLICATIONS

Ruhof Healthcare—Cleaning Solutions for Healthcare Facilities—Ruhof InstruFlush, Retrieved from the Internet, https://www.ruhof.com/products/ruhof-instruflush, on Nov. 2, 2023.

(Continued)

*Primary Examiner* — Donald R Spamer
*Assistant Examiner* — Kayla Rose Sarantakos
(74) *Attorney, Agent, or Firm* — McAfee & Taft

(57) ABSTRACT

A sterilization apparatus has a sterilization chamber in which sterilant gases are produced. A sterilant permeable barrier positioned in the sterilization chamber and a pump is disposed in the sterilant permeable barrier. The pump is operable to pull sterilant gases into the sterilant permeable barrier and to expel the sterilant gases into the sterilant permeable barrier.

18 Claims, 2 Drawing Sheets

(56) References Cited

U.S. PATENT DOCUMENTS

| 6,312,646 | B2 | 11/2001 | Kowanko |
| 6,423,266 | B1 | 7/2002 | Choperena et al. |
| 6,589,481 | B1 * | 7/2003 | Lin ........................... A61L 2/16 |
| | | | 422/305 |
| 6,656,426 | B1 | 12/2003 | Wang et al. |
| 6,936,223 | B2 | 8/2005 | Lippold et al. |
| 6,977,061 | B2 | 12/2005 | Lin et al. |
| 7,229,591 | B2 | 6/2007 | Wu et al. |
| 7,608,218 | B2 | 10/2009 | Fryer et al. |
| 7,703,479 | B2 | 4/2010 | Jacob |
| 7,803,316 | B2 | 9/2010 | Lin et al. |
| 7,999,173 | B1 | 8/2011 | Ashpis |
| 8,480,807 | B2 | 7/2013 | Koster et al. |
| 8,968,651 | B2 | 3/2015 | Hayashi et al. |
| 9,096,932 | B2 | 8/2015 | Savas et al. |
| 9,123,845 | B2 | 9/2015 | Ashpis |
| 9,239,048 | B2 | 1/2016 | Kent et al. |
| 9,848,485 | B2 | 12/2017 | Corke et al. |
| 9,849,202 | B2 | 12/2017 | Jacob et al. |
| 10,426,588 | B2 | 10/2019 | Lam et al. |
| 10,589,114 | B2 | 3/2020 | Pai et al. |
| 11,191,860 | B2 | 12/2021 | Lim et al. |
| 11,246,953 | B2 | 2/2022 | Mermel et al. |
| 2003/0138347 | A1 | 7/2003 | Lin |
| 2008/0260578 | A1 | 10/2008 | Engemann et al. |
| 2009/0127101 | A1 | 5/2009 | Nauman et al. |
| 2010/0147700 | A1 * | 6/2010 | Field ................... A47L 11/4083 |
| | | | 205/687 |
| 2010/0209292 | A1 * | 8/2010 | Hayashi ................. A01N 1/168 |
| | | | 422/186.04 |
| 2012/0196048 | A1 | 8/2012 | Ueda |
| 2013/0064710 | A1 | 3/2013 | Jacob |
| 2013/0119264 | A1 | 5/2013 | Yagi et al. |
| 2013/0147340 | A1 | 6/2013 | Holbeche |
| 2013/0175405 | A1 | 7/2013 | Khozikov et al. |
| 2014/0076712 | A1 | 3/2014 | Jacob et al. |
| 2014/0251787 | A1 | 9/2014 | Montgomery et al. |
| 2015/0206716 | A1 | 7/2015 | Kim et al. |
| 2015/0332897 | A1 | 11/2015 | Tixhon et al. |
| 2015/0374868 | A1 * | 12/2015 | Bruce ....................... A61L 2/07 |
| | | | 422/119 |
| 2015/0380114 | A1 | 12/2015 | Park et al. |
| 2016/0141152 | A1 | 5/2016 | Byrne et al. |
| 2016/0329192 | A1 | 11/2016 | Sieber et al. |
| 2017/0023525 | A1 | 1/2017 | Kubelik et al. |
| 2017/0156379 | A1 * | 6/2017 | Lim ........................ B32B 15/08 |
| 2018/0099149 | A1 | 4/2018 | Pai et al. |
| 2019/0206657 | A1 | 7/2019 | Francesco et al. |
| 2019/0224354 | A1 | 7/2019 | Ma et al. |
| 2019/0373710 | A1 | 12/2019 | Ando et al. |
| 2019/0391387 | A1 | 12/2019 | Neophytou et al. |
| 2020/0006041 | A1 | 1/2020 | Schlemm et al. |
| 2020/0066987 | A1 | 2/2020 | Sims et al. |
| 2020/0236773 | A1 | 7/2020 | Pai et al. |

OTHER PUBLICATIONS

Brochure, Pure Processing, "FlexiPump Independent Flushing System," undated but admitted to be prior art.

Brochure, Plasma Blonics LLC, "V10 Air Plasma Sterilizer," undated but admitted to be prior art.

Plasma Bionics LLC, "Sterilization Wraps," Retrieved from the Internet on Apr. 12, 2022, at https://plasmabionics.com/product/sterilization_wraps/.

Brochure, Plasmapp Co., Ltd., Sterlink FPS-15s (FPS-15s+), User Manual, "Low-temperature plasma sterilizer," revised Jan. 2019.

International Search Report and Written Opinion, issued in corresponding PCT Application No. PCT/US2023/019277 on Sep. 1, 2023.

Pai, Kedar Kamlakant, "Asymmetric Surface Dielectric Barrier Discharge as a Novel Method for Biological Decontamination", Dec. 2015, pp. 1-200.

Sousa, Joao Santos, "Plasma-generated reactive oxygen species for biomedical applications", undated but admitted as prior art, 1 page.

Plasma Sources Science and Technology, "Dielectric barrier discharges: progress on plasma sources and on the understanding of regimes and single filaments", 2017, pp. 1-30.

Fernandez Morales, N., "European Supplementary Search Report for co-pending EP Application No. 1 23792536.7", EP Patent Office, Mar. 9, 2026, pp. 1-9.

* cited by examiner

STERILIZATION APPARATUS

CROSS REFERENCE TO RELATED APPLICATION

The present application claims priority to U.S. Provisional Application No. 63/333,303 filed on Apr. 21, 2022, incorporated herein by reference.

BACKGROUND

This disclosure relates generally to a sterilization apparatus and methods of using the apparatus to sterilize objects. There are a number of different apparatus and methods for sterilizing objects using sterilization chambers. One such sterilization chamber uses plasma, which is a decontamination medium for a number of biological agents. Plasma may be generated, at least in one instance, by applying a differential voltage to electrodes on opposite sides of a dielectric medium. The generation of plasma inside a sealed chamber produces sterilant gases in that chamber. Before proceeding to a description of the present invention it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

DESCRIPTION OF AN EMBODIMENT

Figure 1:
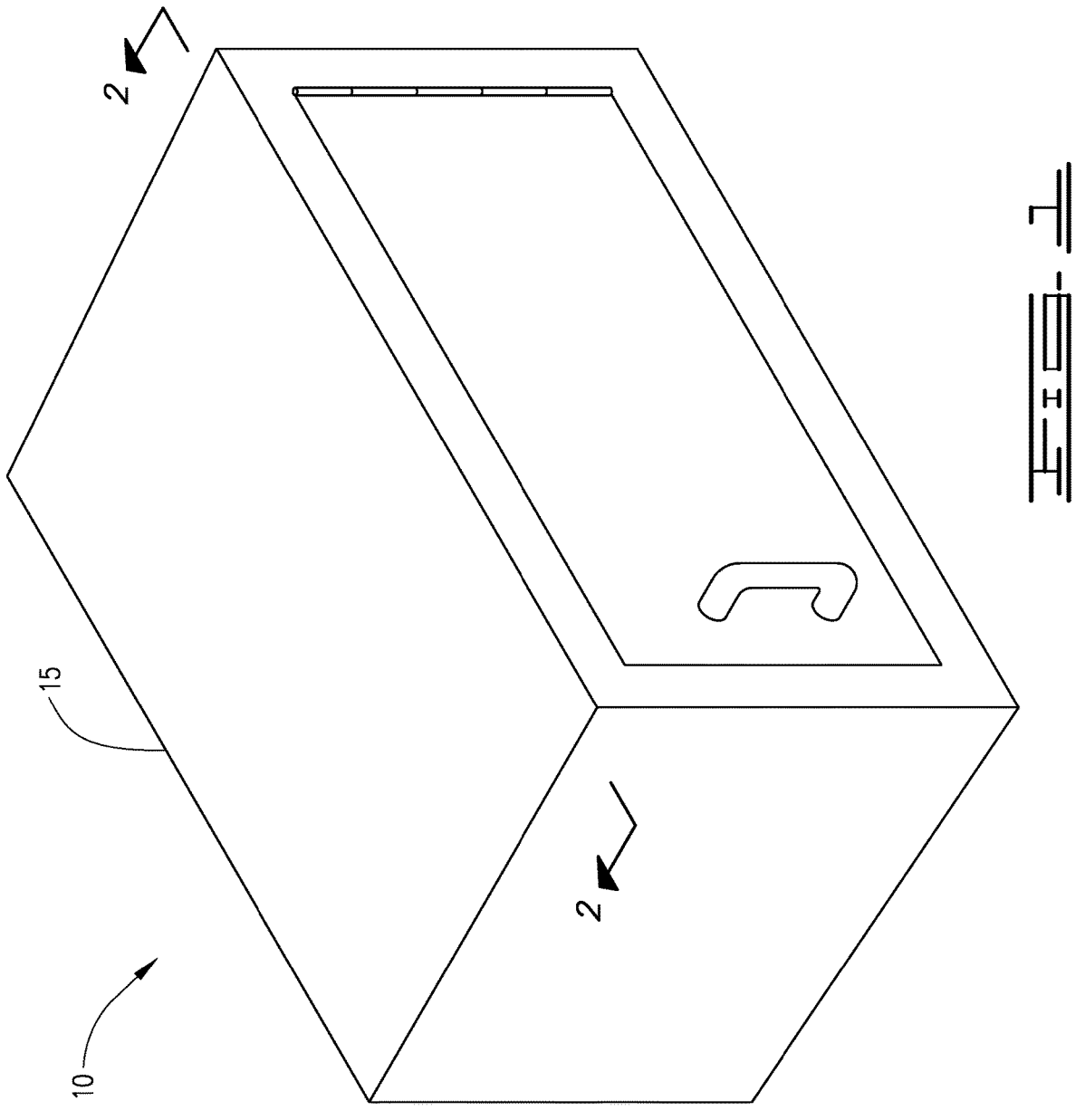
FIG. 1 is a perspective view of a sterilization chamber.
Figure 2:
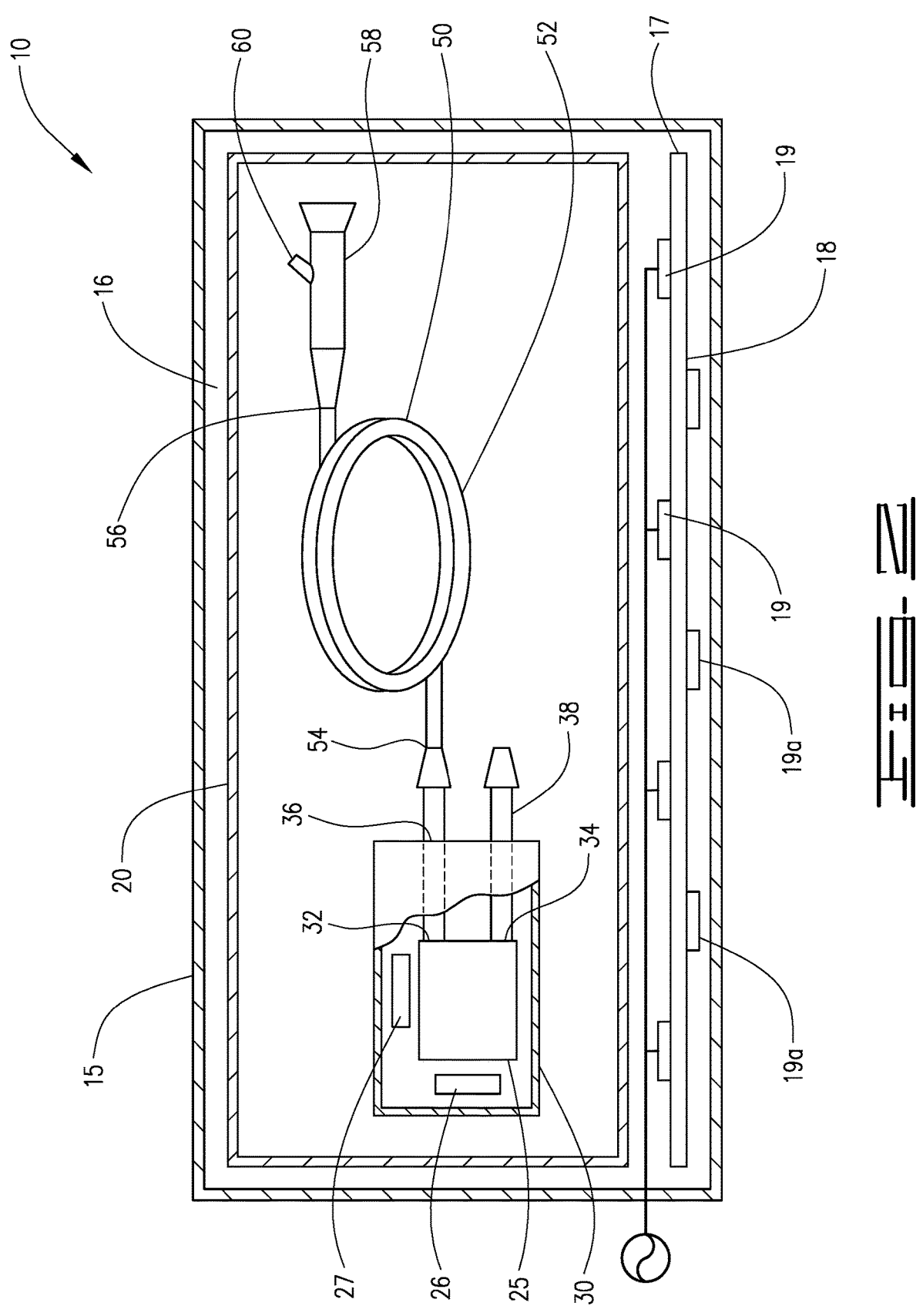
FIG. 2 is a view of the interior of a sterilization chamber of the current disclosure in the direction of line 2-2 on FIG. 1.

In the drawings and description that follow, like parts are typically marked throughout the specification and drawings with the same reference numerals, respectively. In addition, similar reference numerals may refer to similar components in different embodiments disclosed herein. The drawing figures are not necessarily to scale. Certain features may be shown exaggerated in scale or in somewhat schematic form and some details of conventional elements may not be shown in the interest of clarity and conciseness. Specific embodiments are described in detail and are shown in the drawings, with the understanding that the present disclosure is not intended to be limited to the embodiments illustrated and described herein. It is to be fully recognized that the different teachings of the embodiments discussed herein may be employed separately or in any suitable combination to produce desired results.

Unless otherwise specified, use of the terms "connect," "engage," "couple," "attach," or any other like term describing an interaction between elements is not meant to limit the interaction to direct interaction between the elements and may also include indirect interaction between the elements described.

A sterilization apparatus 10 of the current disclosure comprises a sterilization chamber 15 which in the embodiment described is an enclosed chamber. Sterilant gases are produced within, or provided to an interior 16 of chamber 15. One example of a sterilization chamber is a chamber in which gas is produced by placing a plasma sheet 18 inside chamber interior 16. The plasma sheet may include a dielectric medium, which may be referred to as a dielectric barrier and a plurality of first electrodes positioned on a first side of the dielectric medium. The plasma sheet 18 may include a plurality of second electrodes positioned on a second side of the dielectric medium. A power supply is connected to the plasma sheet, for example to the electrodes on one of the first or second sides and is configured to create a voltage differential between the first electrodes and the second electrodes. Plasma is generated on the surface of the plasma sheet, converting air inside chamber 15 into sterilant gases. Thus, only air and electricity are required to generate the sterilant gases inside the chamber 15. The sterilant gases may be for example highly oxidative sterilant gases.

In the described embodiment, plasma sheet 18 may comprise a dielectric barrier 17 with electrodes 19 on a first side thereof and electrodes 19a on a second side thereof. A power source 21 may be connected to the electrodes on at least one side of the plasma sheet, and so may be connected to either of electrodes 19 or 19a. In one embodiment, the electrodes on one side may be coated such that no plasma is generated thereon. In another embodiment, the power source may be connected to the electrodes on one side, for example electrodes 19, and the electrodes 19a on the other side may be connected to a ground so that when power is applied to create a voltage differential plasma is generated on both sides of the dielectric barrier. The generated plasma creates highly oxidative gases known to act as a sterilant.

One example of a chamber 15 which may be utilized as a part of the sterilization apparatus 10 is a V10® AIR PLASMA STERILIZER® made by PLASMA BIONICS® LLC. Plasma is produced from air within the sterilization chamber 15 and is the sole source of sterilant gas generation, with air and electricity being the only inputs for the sterilization process. Multiple ions, charged particles, and reactive oxygen and nitrogen species (such as ozone, nitrogen dioxide, hydroxyl radicals, and nitric oxide, among many others), are produced during the sterilization process. After the sterilization process is complete, the sterilant gases may pass through a catalyst and adsorbent material that converts them back into air. Ozone in particular is produced in high concentrations by the process described and plays an important role in the sterilization efficiency. Singlet oxygen and hydroxyl radicals, both of which are also produced, are the only reactive oxygen species that have a higher oxidation potential.

During the sterilizing step, air inside the sterilization chamber is converted by plasma into multiple reactive oxygen and nitrogen species. The amount of time required for the sterilizing step is defined as twice the amount of time required to kill $10^6$ cells of the most resistant known organism to the process, in this case *Geobacillus stearothermophilus* spores. This provides a sterility assurance level (SAL) of $10^{-6}$. In one embodiment, sterilization in the chamber 15 takes place at 40° C. (104° F.). This is well below the 60° C. (140° F.) required to be classified as a low temperature sterilization method. Heat-sensitive complex instruments composed of plastics and housing sensitive electronics or optics will not be damaged by the sterilization process. The sterilization process occurs at atmospheric pressure. It does not require high pressure like a steam autoclave or a deep vacuum like an ethylene oxide sterilizer. Only a slight variation in pressure (±1 psi) occurs inside the sterilization chamber 15 as the plasma is being produced, which helps push the sterilant gases into hard-to-reach instrument crevices. The minor pressure changes allow even the most delicate instruments to be sterilized without physical damage. While a particular type of sterilization chamber has been described, it is understood that any type of chamber that produces sterilant gases may be utilized.

Sterilization apparatus 10 may further include a sterile barrier 20 positioned in the interior of chamber 15. Sterile barrier 20 may comprise a sterilant permeable barrier which may be for example a Tyvek pouch or SMS wrap. Sterile barrier 20 will be a barrier that prevents micro-organisms from penetrating the barrier while allowing the sterilant gases generated in chamber 15 to easily pass through and contact all parts of devices and/or instruments inside sterile barrier 20.

Sterilization apparatus 10 may further comprise sterilization device 24 placed inside sterile barrier 20. Sterilization device 24 may comprise a pump 25. Pump 25 in one embodiment may be for example a small battery operated pump powered by a battery 26. Other power sources for the pump are possible and battery power is only exemplary. The pump 25 and battery 26 will be fully contained within chamber 15 such that no contamination from outside sources is possible during the sterilization process. In one embodiment pump 25 and battery 26 are fully contained in the sterile barrier. A processor 27 may be included and will be operable to control the power supplied to the pump 25 to conserve battery power and to prevent damage to the pump. In one embodiment pump 25 may have a pump housing 30. Battery 26 and processor 27 may be in pump housing 30 to create a single contained unit. Pump 25 has a pump inlet 32 and a pump outlet 34. A pump inlet conduit 36 may be connected to inlet 32 and a pump outlet conduit 38 may be connected to pump outlet 34. Inlet conduit 36 and outlet conduit 38 will extend outside pump housing 30. When in operation, pump 25 will pull sterilant gas from the interior 16 of the chamber through inlet conduit 36 and will pump sterilant gas back into the interior 16 of chamber 15 through pump outlet conduit 38. A device to be sterilized, for example a hollow tubular device, such as a lumen device 50 may be connected to pump inlet conduit 36. The device may be, in non-limiting examples a laparoscope, endoscope or other device including a lumen. Lumen device 50 may comprise a lumen 52 with a first end 54 and a second end 56. Lumen 52 may include what may be generally referred to as a hand piece 58, or control handle at second end 56. Control portion 58 may have a gas inlet 60 to provide an opening for gas to pass into and through control portion 58 and into lumen 52.

When it is desired to sterilize a lumen device 50, the lumen device 50 along with pump 25 is placed into sterile barrier 20 and sterile barrier 20 is sealed. The sterile barrier 20 with device 50 and pump 25 are placed in the interior 16 of sterilization chamber 15. The pump 25 may be actuated prior to placement in the chamber 15, or may be actuated for example with a remote control after placement in sterilization chamber 15. The processor may be designed so that the remote control will simply activate (i.e., turn the pump 25 on) and deactivate (i.e., turn the pump 25 off). In additional embodiments, the processor 27 can be used to turn the pump on and then off after a predetermined time period, and to turn the pump on and off at defined intervals. Once the pump is activated, sterilant gases from inside sterilization chamber 15 will pass into barrier 20 and pump 25 will pull gas, for example sterilant gas generated in sterilization chamber 15, through lumen device 50 including control portion 58 and lumen 52. The sterilant gases from inside sterilization chamber 15 that pass into sterile barrier 20 are circulated through lumen device 50 for a desired length of time to achieve the desired sterilization of the lumen device 50. Sterilant gas passes through the inlet and outlet conduits 36 and 38 and through pump 25. Sterilant gas passes through no electronic equipment other than pump 25. Sterilization apparatus 10 is designed to provide a sterility assurance level (SAL) of $10^{-6}$ in accordance with the international standard "Sterilization of health care products—General requirements for characterization of a sterilizing agent and the development, validation and routine control of a sterilization process for medical devices" (ISO 14937: 2009). In one embodiment, the amount of time required for the sterilizing step is defined as twice the amount of time required to kill $10^6$ cells of the most resistant known organism to the process, in this case *Geobacillus stearothermophilus* spores. This provides a sterility assurance level (SAL) of $10^{-6}$.

A test was conducted using rigid PTFE (Teflon) tubing 7,620 mm (25 ft) in length and 1 mm (0.039 in) in internal diameter as the lumen. Commercially available self-contained biological indicators (ExpoSure® biological indicators manufactured by Mesa Labs, Inc.), containing at least $10^6$ spores of *Geobacillus stearothermophilus*, were placed inside a container placed at the end of the PTFE tubing and before the device such that the sterilization device 25 pulled sterilant gases through the tubing, then through the container with the biological indicator, and then through sterilization device 24. A total of 4 replicates were repeated with each of 3 separate V10 Air Plasma Sterilizers for a total of 12 replicates. No growth of the spores was observed after 48 hours of incubation for all 12 replicates, indicating a SAL of $10^{-6}$ for the entire length of lumen for all 12 replicates. The length of lumen that can be sterilized is virtually limitless.

Although particular embodiments have been described, sterilization chamber 15 may comprise any chamber in which sterilant gases are produced, or to which sterilant gases are provided. Sterilization device 24 is not limited to any particular pump, battery or processor and any pump and power source that can be placed within the sterile barrier 20 to be placed in a chamber 15 may be utilized. While Tyvek pouches and SMS wraps are provided as examples of a sterile barrier, sterile barrier 20 may comprise any pouch, wrap or other sheath that will permit sterilant gases to pass therethrough, while prohibiting the passage of micro-organisms into the sterile barrier 20. Likewise, while endoscopes and laparoscopes are provided as examples of lumen devices 50 that may be sterilized, it is understood that any lumen and any lumen device can be sterilized with the sterilization apparatus described.

Thus, it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention.

What is claimed is:

1. A sterilization apparatus comprising:
   a sterilization chamber in which sterilant gases are produced;
   a sterilant permeable barrier positioned in the sterilization chamber wherein the sterilant gases are produced inside the sterilization chamber outside the sterilant permeable barrier; and
   a pump having a pump inlet and pump outlet disposed in the sterilant permeable barrier, the pump operable to pull sterilant gases from the sterilant chamber into the sterilant permeable barrier and to expel the sterilant gases into the sterilant permeable barrier.

2. The sterilization apparatus of claim 1 further comprising a lumen device attached to the pump inlet, wherein sterilant gases are pulled through the lumen by the pump.

3. The sterilization apparatus of claim 2, the lumen device being positioned in the sterilant permeable barrier.

4. The sterilization apparatus of claim 1, further comprising a battery positioned in the sterilant permeable barrier, the battery connected to the pump for providing power thereto.

5. The sterilization apparatus of claim 1, the sterilization chamber comprising:
   a plasma sheet disposed in the sealed chamber, the plasma sheet comprising a dielectric barrier with a plurality of electrodes on at least one side thereof; and
   a power source connected to at least some of the electrodes, wherein the application of voltage to at least some of the electrodes generates plasma and plasma generated reactive species in the sterilization chamber.

6. A method of sterilizing a lumen device comprising:
   placing a pump inside a sterilant permeable barrier;
   attaching an end of the lumen device to an inlet of the pump;
   positioning the sterilant permeable barrier, the pump and the lumen device into a sterilization chamber;
   generating sterilant gas inside the sterilization chamber; and
   pulling the sterilant gas through the sterilant permeable barrier and the lumen device.

7. The method of claim 6, further comprising expelling the sterilant gas pulled through the lumen into the sterilant permeable barrier.

8. The method of claim 6 comprising:
   monitoring the sterility assurance level of the lumen; and
   disconnecting the lumen from the pump when a sterility assurance level of $10^{-6}$ is reached.

9. The method of claim 7, wherein the lumen is placed inside the sterilant permeable barrier with the pump.

10. The method of claim 9, further comprising:
   positioning a power source inside the sterilant permeable barrier; and
   connecting the power source to the pump.

11. The method of claim 10, wherein the power source is a battery.

12. The method of claim 11, further comprising placing a processor in the sterilant permeable barrier.

13. The method of claim 12 further comprising:
   electrically connecting the processor to the pump; and
   activating the pump from a location outside the sterilization chamber.

14. A sterilization apparatus comprising:
   a sterilization chamber;
   a sterilant permeable barrier positioned in the sterilization chamber;
   a pump having a pump inlet and a pump outlet disposed in the sterilant permeable barrier; and
   a hollow tubular device positioned in the sterilant permeable barrier and connected to the pump inlet, the pump operable to pull sterilant gas from the sterilization chamber outside the sterilant permeable barrier into the sterilant permeable barrier and through the hollow tubular device through the pump inlet, and to exhaust the sterilant gas through the pump outlet into the sterilant permeable barrier.

15. The sterilization apparatus of claim 14, the hollow tubular device comprising a lumen.

16. The sterilization apparatus of claim 14, further comprising a battery positioned in the sterilant permeable barrier and connected to the pump.

17. The sterilization apparatus of claim 14, wherein the sterilant gas is produced in the sterilization chamber and pulled into the sterilant permeable barrier with the pump.

18. The sterilization apparatus of claim 17, further comprising a microprocessor disposed in the sterilant permeable barrier, the microprocessor operable to actuate the pump upon receiving a signal from a remote control outside the sterilization chamber.

* * * * *